United States Patent [19]
Friedman

[11] Patent Number: 5,514,168
[45] Date of Patent: May 7, 1996

[54] TREATMENT OF VASCULAR HEADACHE AND ATYPICAL FACIAL PAIN

[76] Inventor: Mark H. Friedman, 660 Gramatan Ave., Mt. Vernon, N.Y. 10552

[21] Appl. No.: 246,996

[22] Filed: May 20, 1994

[51] Int. Cl.⁶ .................................................. A61N 5/00
[52] U.S. Cl. .............................................. 607/89; 607/93
[58] Field of Search ........................... 607/88–90, 92–3; 606/2, 13–16

[56] References Cited

U.S. PATENT DOCUMENTS

| | | | |
|---|---|---|---|
| 2,884,926 | 5/1959 | Grasso | 607/92 |
| 4,671,273 | 6/1987 | Lindsey | 607/89 X |
| 4,686,986 | 8/1987 | Fenyo et al. | 607/90 |
| 4,840,174 | 6/1989 | Gluckman | 606/15 |
| 4,852,549 | 8/1989 | Mori | 607/93 X |
| 4,930,504 | 6/1990 | Diamantopoulos et al. | 606/13 X |
| 5,074,860 | 12/1991 | Gregory et al. | 606/14 |
| 5,380,317 | 1/1995 | Everett et al. | 607/89 X |

*Primary Examiner*—Angela D. Sykes
*Attorney, Agent, or Firm*—Evelyn M. Sommer

[57] ABSTRACT

A new method of treatment of vascular headaches (migraine, cluster) as well as atypical pain is presented, comprising the application of bursts of low power laser light to the area of intra-oral tenderness associated with the above conditions. This zone of tenderness is in the area of the plexus formed by the posterior and middle superior alveolar branches of the ipsilateral maxillary nerve. The intra-oral tenderness associated with vascular headaches and facial pain disappears almost immediately, returning in approximately three hours to a few days. With repeated applications, a marked decrease/elimination of the intra-oral tenderness and similar elimination of vascular headache and facial pain frequency and intensity has been observed. The treatment comprises the brief application of bursts of low power laser light (non-cutting 2 mW) from a low-power helium-neon laser, having a maximum output of 5 mW, utilizing an application time of 20 to 30 seconds.

9 Claims, 3 Drawing Sheets

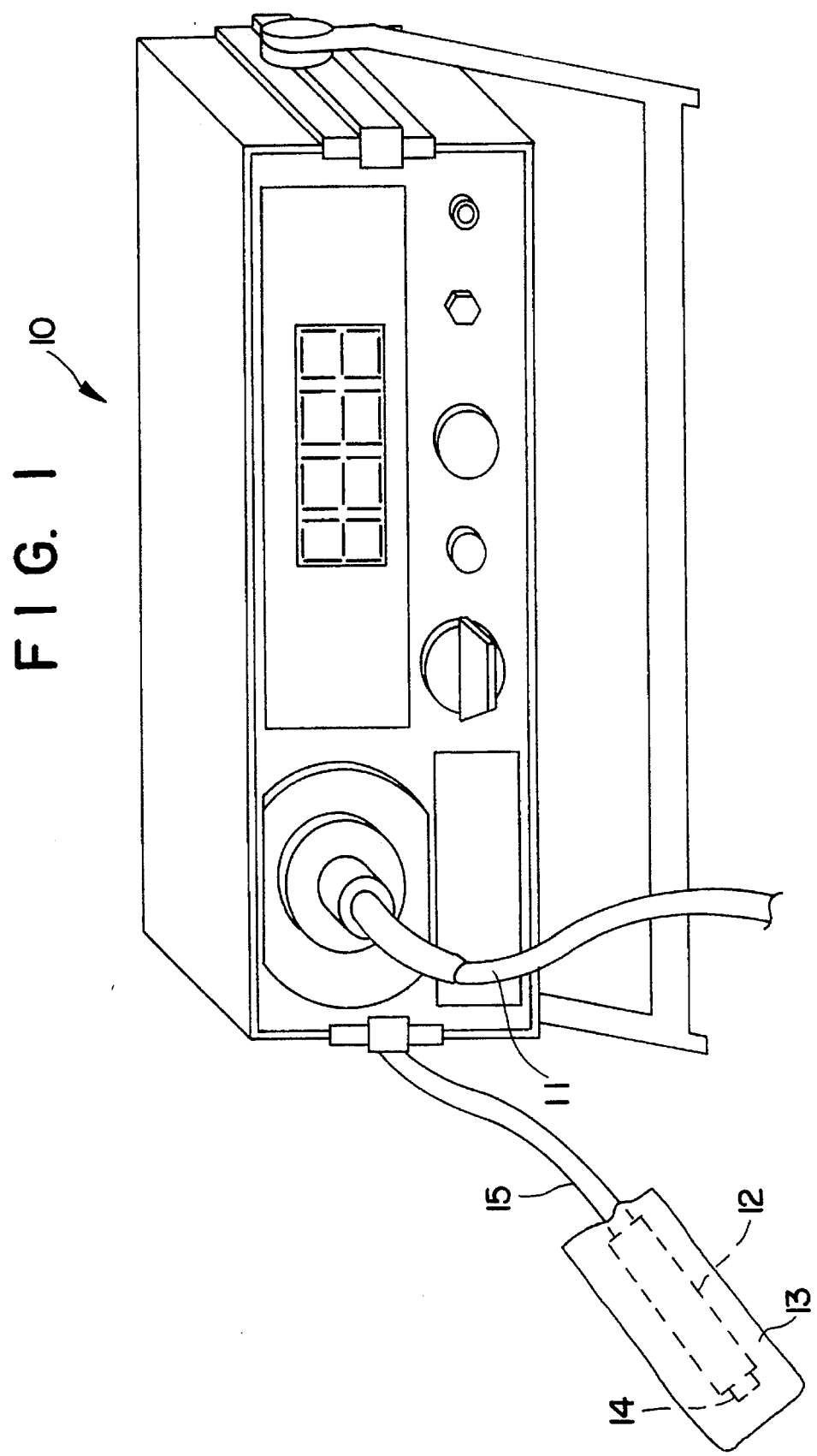

TREATMENT OF VASCULAR HEADACHE AND ATYPICAL FACIAL PAIN

BACKGROUND OF THE INVENTION

The present invention relates to a new method for the treatment of vascular (migraine, cluster) and tension headaches and atypical facial pain.

In accordance with the invention, the method of treatment for these headaches and atypical facial pain consists of the application of bursts of low power laser light to the area of intra-oral tenderness associated with the above conditions. This zone of tenderness is in the area of the plexus formed by the posterior and middle superior alveolar branches of the ipsilateral maxillary nerve. The aforesaid zone of tenderness is located bilaterally when the symptoms are bilateral and unilaterally when the symptoms are one sided.

In the case of tension (muscle contraction) headaches in the frontalis (forehead) and/or orbital region, the laser emitted radiation can also be applied to the supraorbital nerve as it emerges from the supraorbital notch or foramen over the eye. This laser application is performed either separately or in conjunction with the above treatment. The intra-oral tenderness associated with vascular headaches and facial pain disappears immediately after intra-oral laser application, returning in approximately three hours to a few days. With repeated applications, a marked decrease/elimination of the intra-oral tenderness and similar elimination of vascular headache and facial pain frequency and intensity have been observed. Immediate relief is often noted when the patient is symptomatic. In the case of tension headaches, the treatment is usually confined to the symptomatic patient, for immediate relief.

Headaches can be classified into three main groups: vascular (migraine, cluster), muscle contraction (tension), and traction and inflammatory headaches. The latter group may be caused by stroke, hypertension, hemorrhage from an aneurysm, brain tumor, infections, or inflammation.

Migraine is the most common type of headache causing patients to consult a physician. According to the American Council for Headache Education, migraine type headache is reported to occur in 18% of females and 6% of males in the United States. Considering this incidence, the economics of migraine, time lost from work, inefficiency, etc., is substantial. Effective treatment can increase the patient's ability to live a normal and productive life. In addition to pain, the symptoms most commonly associated with migraine include nausea and vomiting, photophobia, phonophobia, pallor, and a desire to lie down. Cluster headaches occur much less frequently than migraines and mostly in men (90%), who usually describe severe unilateral eye pain, associated with ptosis (drooping eyelid), eye tearing, and nasal congestion and/or discharge. These relatively brief but severe headaches occur daily (or more often) during the cluster period, which may last for several months. Atypical facial pain is relatively constant, mostly unilateral, and appears unrelated to jaw function. These patients undergo irreversible dental changes (root canal therapy, multiple extractions) with no appreciable benefit; they respond poorly to all forms of treatment.

Multiple humoral agents have been postulated as being the major factor in migraine. These include serotonin, histamine, prostaglandins, platelet factors, endorphins, and vasoactive neuropeptides. The etiology of migraine has been studied by many investigators. Present research no longer supports the vasodilator/vasoconstrictor mechanism of vascular headache (arterial dilation causes pain and constriction equals relief). Research has now implicated the meninges as the source for vascular head pain, as an unknown trigger activates perivascular trigeminal axons which release vasoactive neuropeptides (substance P, calcitonin gene-related peptide, etc.). These agents produce a local sterile inflammation, causing transmission of impulses to the brain stem and higher centers, for the registration of head pain (Moskowitz MA, Trends in Pharmacological Sciences - August 1992) The intra-oral zone of tenderness located in the area of the root apices of the maxillary molars appears to be the trigger that lowers the threshold for trigeminal axon activation. In the presence of this lowered threshold, various other triggers can cause the headache, for example, hormones, wine, chocolate, changing weather fronts, etc.

Migraine therapy is either prophylactic or symptomatic. Prophylactic medication may be selected for a patient with 2–4 headaches per month, if they are severe enough to interfere with daily activities. Beta blockers such as propranolol (Inderal) are the most common. Other medications, often used, are serotonin antagonists such as methysergide maleate (Sansert), calcium channel blockers (Verapamil), amitriptyline (Elavil), and ergotamine preparations with belladonna alkaloids and phenobarbital. These all have significant side effects such as sedation, loss of energy and drive, dry mouth, constipation, weight gain and gastrointestinal cramping and distress. For symptomatic treatment, ergotamine with caffeine (Cafergot) is commonly used. Other medications include isometheptene mucate (Midrin), NSAID's (Motrin, etc.), dihydroergotamine, and the newer medication sumatriptan (Imitrex) which has to be injected intramuscularly. When narcotics, such as Fiorinal with codeine are frequently used, additional hazards include the considerable potential for rebound headache and habituation.

Cluster headache therapy includes steroids (prednisone), Sansert, various ergot compounds and lithium (for chronic cluster headaches). All of these medications can produce serious side effects and complications. Most neurologists regard atypical facial pain as psychogenic and poorly responsive to all forms of medication. Amitryptaline at bed-time and/or various analgesics and narcotics are commonly used for this condition.

Other modes of treatment for these conditions include: (a) Acupuncture, (b) Biofeedback, and (c) Chiropractic. Acupuncture and chiropractic have been used for headache relief, but studies have failed to show that treatment is much more effective than placebo. Acupuncture requires a highly trained acupuncturist. Biofeedback-training in muscular relaxation may be helpful for muscle contraction headache in selected individuals, but controlled studies have not demonstrated success in the above conditions.

The need for a more appropriate method of treating vascular headaches and atypical facial pain is apparent; the previous methods having often proved ineffective. Treatment with pharmacologic agents is associated with toxicity and must be used systematically. These agents do not meet with patient acceptance or compliance. Migraine headaches represent a tremendous economic loss, considering the number of individuals afflicted, the time lost from work as well as the inability to enjoy a normal pain-free life.

SUMMARY OF THE INVENTION

This invention discloses a method for treating vascular headaches and atypical facial pain involving the application of low power laser beam bursts of energy. Lasers are capable of mobilizing immense heat and power when focused at close range, and are commonly used as a tool in surgical procedures. The term low level or low power, in this application, is used to define lasers that produce no macroscopic tissue changes and no measurable rise in tissue temperature. This application appears particularly effective intra-orally, because the nerves involved lie close to the surface and are not protected by skin. They are covered by a thin layer of mucous membrane.

The application of laser radiation in all of the procedures described herein can be carried out with the conventional apparatus such as an HeNe—laser as for example a so-called low-power or soft laser used for the treatment in various areas such as rheumatology, dermatology, neurology and in dental medicine.

BRIEF DESCRIPTION OF THE DRAWINGS

This invention will be further explained with reference to the drawings wherein:

FIG. 1 is a perspective view of a laser apparatus suitable for use in the invention;

DETAILED DESCRIPTION OF THE DRAWINGS

Figure 2B:
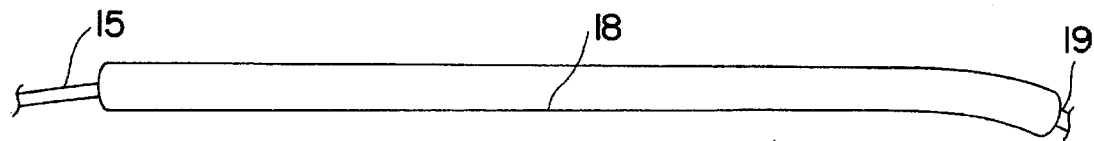
FIG. 2a and b illustrate an embodiment of a new flexible handpiece delivery system suitable for use in the invention.
Figure 2A:
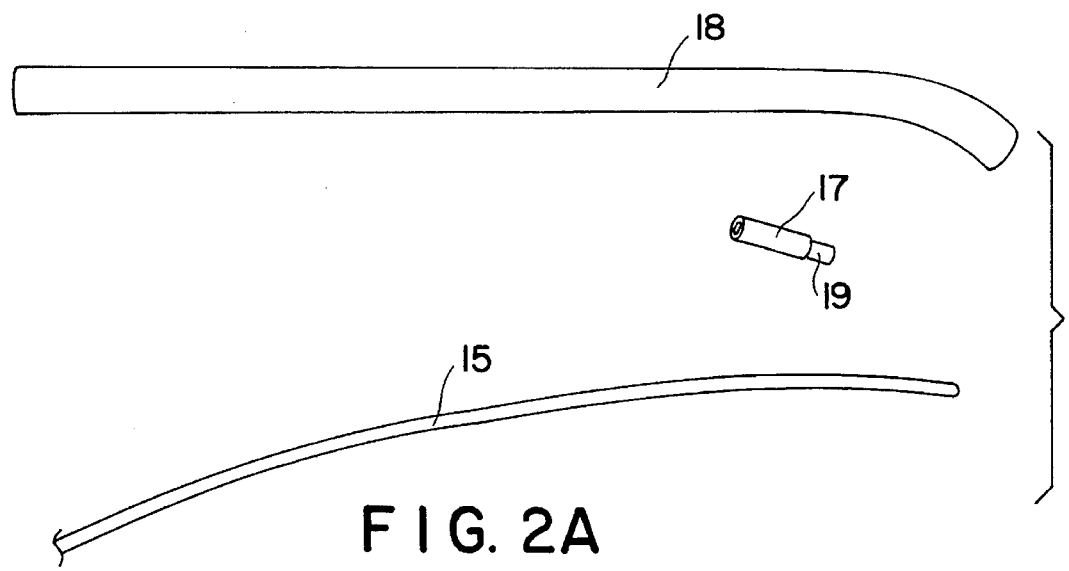

The laser illustrated in FIG. 1 is a conventional low-power Helium-Neon laser—a tube filled with helium and neon. When this mixture is stimulated electrically to emission levels, a beam of light in the visible spectrum (just below infrared) with a wave length of 632.8 nanometers is emitted and allowed to flow through a handheld fiber optic tube for ease of application. The beam is monochromatic, coherent (relative to wave length and form), and non-divergent. The laser 10 in FIG. 1 is powered by normal 110 V current, and has a maximum output of 5 mW. In FIG. 1, 15 represents the fiber optical tube. There is a disposable inner plastic sheath 12 provided with an outer non sterile plastic covering surrounding the optical tube 15 at the point of its contact with the patient. As the energy goes through the fiber optical tube 14, it is reduced to 2 mW at the probe tube 14 which is to be applied to a local point, i.e., the area of tenderness of the patient for treatment. The flexible handpiece delivery system is shown in FIG. 2a wherein 15 designates the optical tube, 18 is a disposable saliva ejector and 14 is a metal delivery tube. In FIG. 2b the parts are shown assembled for use. The delivery tip 17 is comprised of two metal tubes 17 and 19 soldered together. The fiber optic tube goes through both of them and the assembly is inserted within the saliva ejector, with the small metal tube 19 protruding slightly. The large tube 19 serves to prevent slippage within the saliva ejector. The small tube, in addition to allowing the laser beam to issue forth, serves as a tool to record tender areas when pressed against the gingiva. The fiber optical tube and probe can be seen in FIGS. 2a and 2b.

The human nervous system has been demonstrated to be photosensitive, and therapeutic effects relative to pain and wound healing have been reported for the low power laser. Prolonged direct viewing of the laser beam may injure the eye, and patients who are photosensitive probably should not have laser therapy. However, even at doses 75 times that described below, side effects from low level laser therapy have not been reported.

Figure 3:
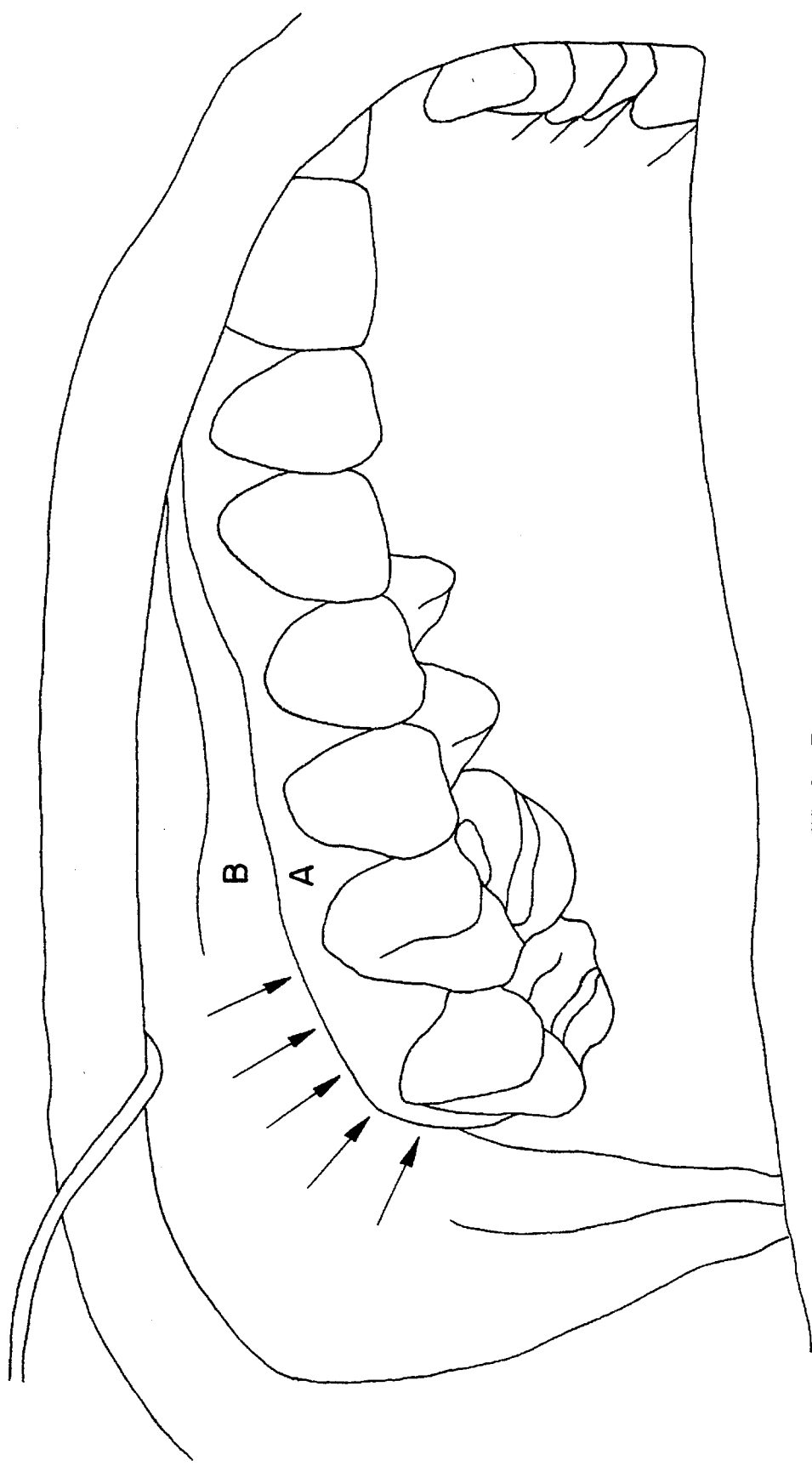
FIG. 3 illustrates the location of the maxillary zone of tenderness intraorally.

An intra-oral zone of tenderness is present over the root apical areas of the posterior maxillary teeth in over 93% of patients with vascular headache (migraine, cluster) and atypical facial pain. This focal tenderness is located on the symptomatic side (bilateral if symptoms are bilateral), and is present even when the patient is symptom free. This area does not represent dental pathology, is radiographically negative, and is not usually noticed by the patient or dentist because of its inaccessibility. The area, usually more tender at its posterior aspect, is located around a nerve plexus formed by branches of the maxillary nerve (FIG. 3). FIG. 3 illustrates the location of the intra-oral zone of maxillary tenderness of one side of the face. The arrows represent the zone of tenderness, A designates the gingiva and B the alveolar mucosa. The posterior alveolar nerves (left and right) arise from the maxillary nerve (the second division of the trigeminal (V) nerve) and descend to form the plexus above the root apices of the maxillary molar teeth. The middle superior alveolar nerves supply the premolar teeth, and sometimes contribute to this plexus.

In order to demonstrate the safety and efficacy of the method of the invention, an investigation was carried out using a considerable number of patients. Using groups of patients with vascular headache (400) and facial pain (25), 376 of the vascular headache patients (94%) and all of the facial pain patients (100%) experienced an immediate elimination or significant reduction of maxillary apical tenderness from brief, (20–30 second) applications of low level (non-cutting laser). A 2 mW helium-neon laser (FIG. 1) was used. In another group of 30 patients, the same results were achieved in 29 patients (96.7%) using 15 second bursts from a 6 mW laser.

The protocol for treatment of a group of 25 patients with atypical facial pain was as follows:

A 30 second application of low-power laser (2 mW helium-neon) to the intra-oral zone of tenderness (FIG. 3) located on the symptomatic side, from proximal to distal in 2–3 mm increments was used. In order to insure sterility, the laser tip was encased in a disposable thin plastic dental handpiece cover; and light tissue contact with the laser tip was maintained. A 30 second exposure was selected for the initial visit because of the clinical observation that longer initial exposures often exacerbated pain. The above procedure was followed for each subsequent visit, with the exception that longer exposures (60–90 seconds) were often used for persistent tenderness. In all cases, reoccurrence or partial reoccurrence of pain and tenderness was reported at the return visit, four to seven days later. To eliminate facial pain, the majority of patients required from one to eight additional treatments (averaging 5.8).

The above treatment is identical for that utilized with vascular headache patients, but requires more visits, averaging approximately eight treatments.

In connection with the above treatment, additional laser treatment was extended to the three foramina i.e., the supraorbital, mandibular, and mental, where the supraorbital, mandibular and mental nerves lie close to the surface (direct laser contact using 30–60 second exposures). Direct laser application reduces/eliminates symptoms by reducing hyperexcitability of the affected nerves. The supraorbital foramen was exposed to the laser for frontal (tension) or vascular headache and anodynia (eye pain) often related to these headaches. The sensory (supraorbital) nerve to the eye and forehead exits at the junction of the medial and middle third of the supraorbital ridge (just under the eyebrow) and is extremely accessible to the laser. The mandibular and mental foramen were exposed to the laser in facial pain patients where symptoms involved the lower jaw.

The results obtained by treating patients with atypical facial pain and vascular headaches follow:

Of the 25 facial pain patients, 16 experienced complete elimination of pain, the results were partially successful in 5, and 4 failed to obtain relief. The five partially successful subjects required additional widely-spaced treatments to maintain symptomatic relief.

The 400 vascular headache patients consist of 380 migraine patients and 20 cluster headache patients. Of the migraine patients, 281 (74%) experienced elimination or significant reduction in headache frequency and/or intensity. Of the 400 migraine patients, 93% were taking medication. Of the successful patients over 90% of those taking medication were able to significantly reduce or eliminate their medication. Of the 20 cluster headache patients, ten (50%) were successful. These figures were arrived at after two to ten weeks of treatment (from two to eight visits). Similar to some of the facial pain patients, many of the successful headache patients required additional widely-spaced treatment to maintain relief. Headache patients with severe cervical dysfunction were not accepted for treatment; those with moderate cervical dysfunction who were accepted also received physical therapy in addition to laser therapy.

Side effects have not been observed in the above patients, nor have any been reported in the literature for other conditions even with more lengthy exposures and with much more powerful lasers (40–60 mW).

I claim:

1. A method of treating vascular headache and atypical facial pain which comprises generating laser radiation utilizing a pulsed HeNe laser including optical fiber means connected to said laser for guiding said laser out from said HeNe laser to the location to be treated comprising an intra-oral area of maxillary tenderness formed by the branches of the maxillary nerve, said optical fiber means terminating in an application probe tip and said laser having a radiation output of 5 mW–10 mW, 50 Hz; placing said probe tip into the mouth of a subject suffering from such condition, adjacent to the area of tenderness associated with the plexus formed by the posterior and middle superior alveolar branches of the ipsilateral maxillary nerve, producing successive pulses of radiation, and conducting said succession of pulses of radiation through said optical fiber means and probe tip so that the radiation impinges on said plexus to at least reduce the subject's symptoms.

2. Method according to claim 1 wherein said subject suffers from vascular headache.

3. Method according to claim 1 wherein said subject suffers from atypical facial pain.

4. Method according to claim 1 wherein the treatment with pulses of radiation has a duration of 20–90 seconds.

5. Method according to claim 1 wherein the treatment with pulses of radiation has a duration of 20–30 seconds.

6. Method according to claim 1 wherein said laser has a maximum output of 5 mW.

7. Method according to claim 6 wherein said laser's output is reduced as it passes through the optical fiber to 2 mW at the probe tip.

8. Method according to claim 1 wherein said applications are made to said zone of tenderness on the symptomatic side, from proximal to distal in 2–3 mm increments.

9. Method according to claim 1 wherein said treatment is repeated at spaced intervals to substantially completely eliminate the pain.

* * * * *